US008951934B2

(12) United States Patent
Schütz et al.

(10) Patent No.: US 8,951,934 B2
(45) Date of Patent: Feb. 10, 2015

(54) ACTIVE COMPOUND COMBINATIONS

(75) Inventors: Burkhard Schütz, Düsseldorf (DE); Peter Dahmen, Neuss (DE); Ulrike Wachendorff-Neumann, Neuwied (DE); Peter Herold, Victoria (AU)

(73) Assignee: Bayer CropScience AG, Monheim (DE)

( * ) Notice: Subject to any disclaimer, the term of this patent is extended or adjusted under 35 U.S.C. 154(b) by 452 days.

(21) Appl. No.: 13/140,287

(22) PCT Filed: Dec. 5, 2009

(86) PCT No.: PCT/EP2009/008698
§ 371 (c)(1),
(2), (4) Date: Jun. 16, 2011

(87) PCT Pub. No.: WO2010/069489
PCT Pub. Date: Jun. 24, 2010

(65) Prior Publication Data
US 2011/0251062 A1    Oct. 13, 2011

(30) Foreign Application Priority Data

Dec. 19, 2008  (EP) .................................. 08172309

(51) Int. Cl.
A01N 43/80    (2006.01)
A01N 43/40    (2006.01)
A01N 43/88    (2006.01)
A01N 37/50    (2006.01)
A01N 43/10    (2006.01)
A01N 43/78    (2006.01)
A01N 43/82    (2006.01)

(52) U.S. Cl.
CPC .............. A01N 43/10 (2013.01); A01N 43/78 (2013.01); A01N 43/80 (2013.01); A01N 43/82 (2013.01)
USPC ........ 504/100; 514/229.2; 514/345; 514/372; 514/407; 514/539; 514/619

(58) Field of Classification Search
USPC ............... 504/100; 514/372, 539, 229.2, 345, 514/407, 619
See application file for complete search history.

(56) References Cited

U.S. PATENT DOCUMENTS

| 4,245,432 | A |   | 1/1981 | Dannelly |
| 4,272,417 | A |   | 6/1981 | Barke et al. |
| 4,808,430 | A |   | 2/1989 | Kouno |
| 5,240,951 | A |   | 8/1993 | Shimotori et al. |
| 5,876,739 | A |   | 3/1999 | Turnblad et al. |
| 6,166,054 | A | * | 12/2000 | Kuroda et al. ............ 514/361 |
| 6,191,155 | B1 |   | 2/2001 | Assmann et al. |
| 7,774,978 | B2 |   | 8/2010 | Ding et al. |
| 2002/0091067 | A1 |   | 7/2002 | Assmann et al. |
| 2003/0176428 | A1 |   | 9/2003 | Schneidersmann et al. |
| 2004/0204470 | A1 |   | 10/2004 | Elbe et al. |
| 2007/0066562 | A1 |   | 3/2007 | Dahmen et al. |
| 2008/0200457 | A1 |   | 8/2008 | Umetani et al. |
| 2008/0269051 | A1 |   | 10/2008 | Suty-Heinze et al. |
| 2009/0018015 | A1 |   | 1/2009 | Wachendorff-Neumann et al. |
| 2011/0105331 | A1 |   | 5/2011 | Ebbinghaus et al. |
| 2011/0251062 | A1 |   | 10/2011 | Schütz et al. |

FOREIGN PATENT DOCUMENTS

| EP | 1 175 834 A1 | 1/2002 |
| JP | 6-9313 A | 1/1994 |
| WO | WO 96/29871 A2 | 10/1996 |
| WO | WO 99/24413 A2 | 5/1999 |
| WO | WO 02/28186 A2 | 4/2002 |
| WO | WO 02/080675 A1 | 10/2002 |
| WO | WO 2005/009130 A1 | 2/2005 |
| WO | WO 2005/041653 A2 | 5/2005 |
| WO | WO 2006/040123 A2 | 4/2006 |

OTHER PUBLICATIONS

Bartlett, D.W. et al., "The strobilurin fungicides," Pest Management Science, vol. 58, pp. 649-662 (2002).*
Notice of Allowance mailed May 9, 2013, in co-pending U.S. Appl. No. 12/934,836, § 371(c) Date: Dec. 17, 2010, U.S. Patent and Trademark Office, Alexandria, VA.
Bauer, T.A., et al., "Response of Selected Weed Species to Postemergence Imazethapyr and Bentazon," Weed Tech. 9:236-242, The Weed Science Society of America, United States (1995).
Blackshaw, R.E., "HOE-39866 Use in Chemical Fallow Systems," Weed Tech. 3:420-428, The Weed Science Society of America, United States (1989).
Blackshaw, R.E., "Synergistic Mixes of DPX-A7881 and Clopyralid in Canola (Brassica napus),"Weed Tech. 3:690-695, The Weed Science Society of America, United States (1989).
Blackshaw, R.E., et al., "Herbicide Combinations for Postemergent Weed Control in Safflower (Carthamus tinctorius)," Weed Tech. 4:97-107, The Weed Science Society of America, United States (1990).
Blouin, D.C., et al., "Analysis of Synergistic and Antagonistic Effects of Herbicides Using Nonlinear Mixed-Model Methodology," Weed Tech. 18:464-472, The Weed Science of America, United States (2004).
Bradley, P.R., et al., "Response of Sorghum (Sorghum bicolor) to Atrazine, Ammonium Sulfate, and Glyphosate," Weed Tech. 14:15-18, The Weed Science Society of America, United States (2000).

(Continued)

Primary Examiner — John Pak
(74) Attorney, Agent, or Firm — Sterne, Kessler, Goldstein & Fox P.L.L.C.

(57) ABSTRACT

The invention relates to active compound combinations, in particular within a fungicide composition, which comprises (A) a compound of formula (I) and at least one further respiratory chain complex in inhibitor (B). Moreover, the invention relates to a method for curatively or preventively controlling the phytopathogenic fungi of plants or crops, to the use of a combination according to the invention for the treatment of seed, to a method for protecting a seed and not at least to the treated seed.

13 Claims, No Drawings

(56) References Cited

OTHER PUBLICATIONS

Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).

Burke, I.C., et al., "CGA-362622 Antagonizes Annual Grass Control with Clethodim," *Weed Tech.* 16:749-754, The Weed Science Society of America, United States (2002).

Colby, S.R., "Calculating Synergistic and Antagonistic Responses of Herbicide Combinations," *Weeds* 15:20-22, Weed Society of America, United States (1967).

Crickmore, N., et al., "Revision of the Nomenclature for the *Bacillus thuringiensis* Pesticidal Crystal Proteins," *Microbiology and Molecular Biology Reviews* 62(3):807-813, American Society for Microbiology, United States (1998).

Flint, J.L., et al., "Analyzing Herbicide Interactions: A Statistical Treatment of Colby's Method," *Weed Tech.* 2:304-309, The Weed Science Society of America, United States (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, K.N. and O'Sullivan, A., "Synergistic Mixtures of Sethoxydim and Fluazifop on Annual Grass Weeds," *Weed Tech.* 5:310-316, The Weed Science Society of America, United States (1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions Between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosphate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," *Weed Science* 23:4-6, The Weed Science Society of America, United States (1975).

Salzman, F.P. and Renner, K.A., "Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects on Synergism from Post-Applied Tank Mixtures of SAN 582H Fluzaifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E. and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

English language Abstract of Japanese Patent Publication No. 06-009313 A, Japanese Patent Office, Patent & Utility Model Gazette DB, Patent Abstracts of Japan, (1994).

International Search Report for International Application No. PCT/EP2009/008698, European Patent Office, The Hague, Netherlands, mailed on Jan. 20, 2010.

Office Action co-pending U.S. Appl. No. 12/934,836, § 371(c) Date: Dec. 17, 2010, U.S. Patent and Trademark Office, Alexandria, VA, mailed Nov. 15, 2011.

Office Action co-pending U.S. Appl. No. 12/934,836, § 371(c) Date: Dec. 17, 2010, U.S. Patent and Trademark Office, Alexandria, VA, mailed Apr. 27, 2012.

Office Action co-pending U.S. Appl. No. 12/934,836, § 371(c) Date: Dec. 17, 2010, U.S. Patent and Trademark Office, Alexandria, VA, mailed Jul. 2, 2012.

Office Action co-pending U.S. Appl. No. 12/934,836, § 371(c) Date: Dec. 17, 2010, U.S. Patent and Trademark Office, Alexandria, VA, mailed Sep. 19, 2012.

\* cited by examiner

ACTIVE COMPOUND COMBINATIONS

The invention relates to active compound combinations, in particular within a fungicide composition, which comprises (A) at least one compound according to formula (I)

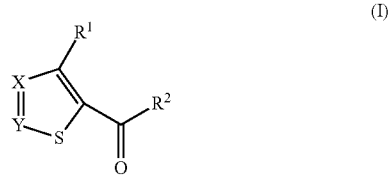

wherein
X is selected from nitrogen and C-Hal,
Y is selected from nitrogen and C-Hal,
$R^1$ is selected from hydrogen, halogen, $C_1$-$C_6$ alkyl substituted with Hal, $C_2$-$C_6$ alkenyl substituted with Hal, $C_3$-$C_6$ cycloalkyl substituted with Hal, phenyl which is substituted with one or more substituents selected from the group of halogen, cyano, and alkoxy,
$R^2$ is selected from hydroxy, $C_1$-$C_6$ thioalkyl, $C_1$-$C_6$ aminoalkyl,
$C_1$-$C_6$ alkoxy which is substituted with one or more substituents selected from the group of halogen, cyano, $C_1$-$C_6$ alkoxy, $C_1$-$C_6$ alkyl, $C_1$-$C_6$ alkylcarbonyl,
phenoxy which is substituted with one or more substituents selected from the group of with halogen, cyano, alkoxy, $C_1$-$C_6$ alkyl, alkylamino, formyl, $C_1$-$C_6$ alkoxy, $C_1$-$C_6$ alkylcarbonyl, $C_1$-$C_6$ alkoxycarbonyl,
aniline which is substituted with one or more substituents selected from the group of cyano, halogen, $C_1$-$C_6$ alkyl, $C_1$-$C_6$ alkoxy, $C_1$-$C_6$ alkylcarbonyl,
Hal is halogen,
and at least one fungicidally active compound (B) selected from the group
comprising of (B1) members of the strobilurin group as selected from Trifloxystrobin, Dimoxystrobin, Fluoxastrobin, Pyraclostrobin, Enestroburin, Picoxystrobin,
comprising of (B2) members of the azole group as selected from Epoxiconazole, Triticonazole, Ipconazole, Difenoconazole, Diniconazole, Hymexazole, Metconazole, Simeconazole, Triflumizole,
comprising of (B3) members of the carboxamide group as selected from N-[2-(1,3-Dimethylbutyl)phenyl]-5-fluor-1,3-dimethyl-1H-pyrazole-4-carboxamide (known from WO 03/010149), Bixafen, Sedexane, Fluopyram, Boscalid, Carboxin
comprising of (B4) members of the other fungicides group as selected from Prochloraz, Carbendazim, Thiram, Fluopicolide, Fenamidone, Fludioxinil, Metalaxyl, Mefenoxam, MTF-154 (Mitsui), Zoxamide, Furametanyl, Tecloftalam, Oxolinic-acid, Chlorothalonil, Metalaxyl, Etridiazole, Thiophanate-methyl, Thiram, Benomyl, Copper, Copper-oxychloride, Validamycin, Ferimzone.

Moreover, the invention relates to a method for curatively or preventively controlling the phytopathogenic fungi of plants or crops, to the use of a combination according to the invention for the treatment of seed, to a method for protecting a seed and not at least to the treated seed.

It is already known that the compounds according to formula (I) are highly suitable for protecting plants against attack by undesirable phytopathogenic fungi and microorganisms (WO 99/024 413, WO 2006/098128, JP 2007-84566, WO 96/29871 U.S. Pat. No. 5,240,951 and JP-A 06-009313). The compound (A) Isotianil according to the invention is suitable both for mobilizing the defenses of the plant against attack by undesirable phytopathogenic fungi and microorganisms and as microbicides for the direct control of phytopathogenic fungi and microorganisms. In addition, the compound (A) is also active against pests which damage plants (WO 99/24414). In addition, combinations of Isotianil with selected fungicides have been described in WO 2005/009130. The activity of this substance is good; however, at low application rates it is in some cases unsatisfactory.

Since, moreover, the environmental and economic requirements imposed on modern-day fungicides are continually increasing, with regard, for example, to the spectrum of action, toxicity, selectivity, application rate, formation of residues, and favourable preparation ability, and since, furthermore, there may be problems, for example, with resistances, a constant task is to develop new fungicide agents which in some areas at least have advantages over their known counterparts.

The invention provides active compound combinations/compositions which in some aspects at least achieve the stated objectives.

It has now been found, surprisingly, that the combinations according to the invention not only bring about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the combination still achieves a high degree of phytopathogen control even where the two individual compounds have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal activity, the pesticidal combinations according to the invention also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; adequate pest control with the aid of the compositions according to the invention, even at a rate of application at which the individual compounds are totally ineffective;

advantageous behaviour during formulation or upon application, for example upon grinding, sieving, emulsifying, dissolving or dispensing; increased storage stability; improved stability to light; more advantageuos degradability; improved toxicological or ecotoxicological behaviour; improved characteristics of the useful plants including: emergence, crop yields, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The combination according to the invention can also provide an improved systemicity to the active compounds that are used. Indeed, even if some of the used fungicide compounds do not possess any or a satisfying systemicity, within the composition according to the invention these compounds can exhibit such a property.

In a similar manner, the combination according to the invention can allow an increased persistence of the fungicide efficacy of the active compounds that are employed.

Another advantage of the combination according to the invention relies in that an increased curativity is achievable.

Accordingly, the present invention provides a combination comprising:

(A) at least one compound according to formula (1)

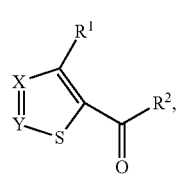

(I)

wherein
X is selected from nitrogen and C-Hal,
Y is selected from nitrogen and C-Hal,
$R^1$ is selected from hydrogen, halogen, $C_1$-$C_6$ alkyl substituted with Hal, $C_2$-$C_6$ alkenyl substituted with Hal, $C_3$-$C_6$ cycloalkyl substituted with Hal, phenyl which is substituted with one or more substituents selected from the group of halogen, cyano, and alkoxy,
$R^2$ is selected from hydroxy, $C_1$-$C_6$ thioalkyl, $C_1$-$C_6$ aminoalkyl,
$C_1$-$C_6$ alkoxy which is substituted with one or more substituents selected from the group of halogen, cyano, $C_1$-$C_6$ alkoxy, $C_1$-$C_6$ alkyl, $C_1$-$C_6$ alkylcarbonyl,
phenoxy which is substituted with one or more substituents selected from the group of with halogen, cyano, alkoxy, $C_1$-$C_6$ alkyl, $C_1$-$C_6$ alkylamino, formyl, $C_1$-$C_6$ alkoxy, $C_1$-$C_6$ alkylcarbonyl, $C_1$-$C_6$ alkoxycarbonyl,
aniline which is substituted with one or more substituents selected from the group of cyano, halogen, $C_1$-$C_6$ alkyl, $C_1$-$C_6$ alkoxy, $C_1$-$C_6$ alkylcarbonyl,
Hal is halogen
and
(B) and at least one fungicidally active compound (B) selected from the group
comprising of (B1) members of the strobilurin group as selected from Trifloxystrobin (141517-21-7), Dimoxystrobin (141600-52-4), Fluoxastrobin (361377-29-9), Pyraclostrobin (175013-18-0), Enestroburin (238410-11-2), Picoxystrobin (117428-22-5),
comprising of (B2) members of the azo group as selected from Epoxiconazole (106325-08-0), Triticonazole (131983-72-7), Ipconazole (125225-28-7), Difenoconazole (119446-68-3), Diniconazole (83657-24-3), Hymexazole (10004-44-1), Metconazole (125116-23-6), Simeconazole (149508-90-7), Triflumizole (68694-11-1),
comprising of (B3) members of the carboxamide group as selected from N-[2-(1,3-Dimethylbutyl)phenyl]-5-fluor-1,3-dimethyl-1H-pyrazole-4-carboxamide (known from WO 03/010149), Bixafen (581809-46-3), Sedexane, Fluopyram (658066-35-4), Boscalid (188425-85-6), Carboxin (5234-68-4),
comprising of (B4) members of the other fungicides group as selected from Prochloraz (67747-09-5), Carbendazim (10605-21-7), Thiram (137-26-8), Fluopicolide (239110-15-7), Fenamidone (161326-34-7), Fludioxinil (131341-86-1), Metalaxyl (57837-19-1), Mefenoxam (70630-17-0), MTF-154 (Mitsui), Zoxamide (156052-68-5), Furametanyl, Tecloftalam (76280-91-6), Oxolinic-acid (14698-29-4), Chlorothalonil (1897-45-6), Etridiazole (2593-15-9), Thiophanate-methyl (23564-05-8), Benomyl (17804-35-2), Copper, Copper-oxychloride (1332-40-7), Validamycin (37248-47-8), Ferimzone (89269-64-7).

Preference is given to combinations comprising (A) at least one compound of the formula (I),

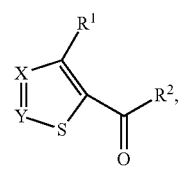

(I)

wherein
X is selected from nitrogen and C-Hal,
Y is nitrogen,
$R^1$ is selected from halogen, $C_1$-$C_6$ alkyl substituted with Hal, $C_2$-$C_6$ alkenyl substituted with Hal, $C_3$-$C_6$ cycloalkyl substituted with Hal,
$R^2$ is selected from hydroxy, $C_1$-$C_6$ thioalkyl, $C_1$-$C_6$ aminoalkyl,
$C_1$-$C_6$ alkoxy which is substituted with one or more substituents selected from the group of halogen, cyano, $C_1$-$C_6$ alkoxy, $C_1$-$C_6$ alkyl, $C_1$-$C_6$ alkylcarbonyl,
phenoxy which is substituted with one or more substituents selected from the group of with halogen, cyano, alkoxy, $C_1$-$C_6$ alkyl, $C_1$-$C_6$ alkylamino, formyl, $C_1$-$C_6$ alkoxy, $C_1$-$C_6$ alkylcarbonyl, $C_1$-$C_6$ alkoxycarbonyl,
aniline which is substituted with one or more substituents selected from the group of cyano, halogen, $C_1$-$C_6$ alkyl, $C_1$-$C_6$ alkoxy, $C_1$-$C_6$ alkylcarbonyl,
Hal is fluorine, chlorine, bromine.

Particular preference is given to combinations comprising (A) at least one compound of the formula (I), wherein Hal is chlorine or bromine.

Particular preference is given to combinations comprising (A) at least one compound of the formula (I), wherein Hal is chlorine.

Particular preference is given to combinations comprising (A) at least one compound of the formula (I), wherein X is C-Hal or nitrogen and Y is nitrogen.

Particular preference is given to combinations comprising (A) at least one compound of the formula (I), wherein X is C-Hal and Y is nitrogen.

Particular preference is given to combinations comprising (A) at least one compound of the formula (I), wherein X is nitrogen and Y is nitrogen.

Particular preference is given to combinations comprising (A) at least one compound of the formula (I), wherein X is C-Hal or nitrogen and Y is nitrogen and $R^2$ is aniline which is substituted with one or more substituents selected from the group of cyano, halogen, $C_1$-$C_6$ alkyl, $C_1$-$C_6$ alkoxy, $C_1$-$C_6$ alkylcarbonyl.

Particular preference is given to combinations comprising (A) at least one compound of the formula (I), wherein X is C-Hal or nitrogen and Y is nitrogen and $R^2$ is hydroxy.

Particular preference is given to combinations comprising (A) at least one compound of the formula (I), wherein X is C-Hal and Y is nitrogen and $R^2$ is hydroxy.

Particular preference is given to combinations comprising (A) at least one compound of the formula (I), wherein X is nitrogen and Y is nitrogen and $R^2$ is hydroxy.

Particular preference is given to combinations comprising (A) at least one compound of the formula (I), wherein X is C-Hal or nitrogen and Y is nitrogen and $R^2$ is $C_1$-$C_6$ thioalkyl.

Particular preference is given to combinations comprising (A) at least one compound of the formula (I), according to table 1:

TABLE 1

| No  | X     | Y | $R^1$       | $R^2$                   | Hal |
|-----|-------|---|-------------|-------------------------|-----|
| I-1 | N     | N | $CH_3$      | 3-chloro-4-methyl aniline | —   |
| I-2 | C—Hal | N | Cl          | 2-cyano aniline         | Cl  |
| I-3 | N     | N | $CH_3$      | OH                      | —   |
| I-4 | C—Hal | N | Cl          | OH                      | Cl  |
| I-5 | N     | N | cyclopropyl | 3-chloro-4-methyl aniline | —   |

According to the invention, "alkyl" represents straight-chain or branched aliphatic hydrocarbons having 1 to 6, preferably 1 to 4 carbon atoms, most preferably having 1 to 3 carbon atoms. Preferred alkyl groups are, for example, methyl, ethyl, n-propyl, i-propyl, n-, iso-, sec- or tert-butyl, pentyl or hexyl.

According to the invention, "alkenyl" represents straight-chain or branched hydrocarbons having at least one double bond. The double bond of the alkenyl group may be unconjugated or is conjugated to an unsaturated bond or group. Alkenyl groups having 2 to 6 or 3 to 6 carbon atoms are preferred. Preferred alkenyl groups are, for example, vinyl or allyl.

According to the invention, "halogen" represents fluorine, chlorine, bromine or iodine, preferably fluorine, chlorine or bromine, most preferably bromine and chlorine.

According to the invention, "cycloalkyl" represents cyclic hydrocarbons having 3 to 6 carbon atoms. Preferred cycloalkyl groups are, for example, cyclopropyl, cyclobutyl, cyclopentyl or cyclohexyl.

According to the invention, "alkoxy" represents alkoxy groups having 1 to 6 carbon atoms, preferably having 1 to 4 carbon atoms, most preferably having 1 to 3 carbon atoms. Preferred alkoxy groups are, for example, methyloxy, ethyloxy, n-propyloxy, i-propyloxy, n-, iso-, sec- or tert-butyloxy, pentyloxy or hexyloxy.

According to the invention, "alkoxycarbonyl" represents alkoxycarbonyl groups having 1 to 6 carbon atoms, preferably having 1 to 4 carbon atoms, most preferably having 1 to 3 carbon atoms. Preferred alkoxycarbonyl groups are, for example, methyloxycarbonyl, ethyloxycarbonyl, n-propyloxycarbonyl, i-propyloxycarbonyl, n-, iso-, sec- or tert-butyloxycarbonyl, pentyloxycarbonyl or hexyloxycarbonyl.

According to the invention, "alkylcarbonyl" represents alkylcarbonyl groups having 1 to 6 carbon atoms, preferably having 1 to 4 carbon atoms, most preferably having 1 to 3 carbon atoms. Suitable alkyl groups are, for example, methylcarbonyl, ethylcarbonyl, n-propylcarbonyl, i-propylcarbonyl, n-, iso-, sec- or tert-butylcarbonyl, pentylarbonyl or hexylcarbonyl.

The above-mentioned definitions either in the general description or in the preferred embodiments can be combined between the respective embodiments and preferred embodiments.

Halogen stands for fluorine, chlorine, bromine and iodine. Fluorine, chlorine, and bromine are preferred, Bromine and chlorine are particularly preferred.

The above-mentioned definitions either in the general description or in the preferred embodiments can be combined between the respective embodiments and preferred embodiments.

Preference is further given to combinations comprising compounds (B) selected from the list comprising of (B1) members of the strobilurin group as selected from Trifloxystrobin, Dimoxystrobin, Fluoxastrobin, Pyraclostrobin, Enestroburin, Picoxystrobin.

Preference is further given to combinations comprising compounds (B) selected from the list comprising of (B2) members of the azo group as selected from Epoxiconazole, Triticonazole, Ipconazole, Difenoconazole, Diniconazole, Hymexazole, Metconazole, Simeconazole, Triflumizole, Preference is further given to combinations comprising compounds (B) selected from the list comprising of (B3) members of the carboxamide group as selected from N-[2-(1,3-Dimethylbutyl)phenyl]-5-fluor-1,3-dimethyl-1H-pyrazole-4-carboxamide (known from WO 03/010149), Bixafen, Sedexane, Fluopyram, Boscalid, Carboxin Preference is further given to combinations comprising compounds (B) selected from the list comprising of (B4) members of the other fungicides group as selected from Prochloraz, Carbendazim, Thiram, Fluopicolide, Fenamidone, Fludioxinil, Metalaxyl, Mefenoxam, MTF-154 (Mitsui), Zoxamide, Furametanyl, Tecloftalam, Oxolinic-acid, Chlorothalonil, Metalaxyl, Etridiazole, Thiophanate-methyl, Thiram, Benomyl, Copper, Copper-oxychloride, Validamycin, Ferimzone.

For most of the compounds of group (B) we refer to The Pesticide Manual, $13^{th}$ edition, 2003.

Particularly preferred combinations are listed below:

(A) compound I-1 and (B) Trifloxystrobin, (A) compound I-2 and (B) Trifloxystrobin, (A) compound I-3 and (B) Trifloxystrobin, (A) compound I-4 and (B) Trifloxystrobin, (A) compound I-5 and (B) Trifloxystrobin (A) compound I-1 and (B) Dimoxystrobin, (A) compound I-2 and (B) Dimoxystrobin, (A) compound I-3 and (B) Dimoxystrobin, (A) compound I-4 and (B) Dimoxystrobin, (A) compound I-5 and (B) Dimoxystrobin (A) compound I-1 and (B) Fluoxastrobin, (A) compound I-2 and (B) Fluoxastrobin, (A) compound I-3 and (B) Fluoxastrobin, (A) compound I-4 and (B) Fluoxastrobin, (A) compound I-5 and (B) Fluoxastrobin (A) compound I-1 and (B) Pyraclostrobin, (A) compound I-2 and (B) Pyraclostrobin, (A) compound I-3 and (B) Pyraclostrobin, (A) compound I-4 and (B) Pyraclostrobin, (A) compound I-5 and (B) Pyraclostrobin (A) compound I-1 and (B) Enestroburin, (A) compound I-2 and (B) Enestroburin, (A) compound I-3 and (B) Enestroburin, (A) compound I-4 and (B) Enestroburin, (A) compound I-5 and (B) Enestroburin (A) compound I-1 and (B) Picoxystrobin, (A) compound I-2 and (B) Picoxystrobin, (A) compound I-3 and (B) Picoxystrobin, (A) compound I-4 and (B) Picoxystrobin, (A) compound I-5 and (B) Picoxystrobin (A) compound I-1 and (B) Epoxiconazole, (A) compound I-2 and (B) Epoxiconazole, (A) compound I-3 and (B) Epoxiconazole, (A) compound I-4 and (B) Epoxiconazole, (A) compound I-5 and (B) Epoxiconazole (A) compound I-1 and (B) Triticonazole, (A) compound I-2 and (B) Triticonazole, (A) compound I-3 and (B) Triconazole, (A) compound I-4 and (B) Triticonazole, (A) compound I-5 and (B) Triticonazole
(A) compound I-1 and (B) Ipconazole, (A) compound I-2 and (B) Ipconazole, (A) compound I-3 and (B) Ipconazole, (A) compound I-4 and (B) Ipconazole, (A) compound I-5 and (B) Ipconazole
(A) compound I-1 and (B) Difenoconazole, (A) compound I-2 and (B) Difenoconazole, (A) compound I-3 and (B) Difenoconazole, (A) compound I-4 and (B) Difenoconazole, (A) compound I-5 and (B) Difenoconazole
(A) compound I-1 and (B) Diniconazole, (A) compound I-2 and (B) Diniconazole, (A) compound I-3 and (B) Diniconazole, (A) compound I-4 and (B) Diniconazole, (A) compound I-5 and (B) Diniconazole
(A) compound I-1 and (B) Hymexazole, (A) compound I-2 and (B) Hymexazole, (A) compound I-3 and (B) Hymexazole, (A) compound I-4 and (B) Hymexazole, (A) compound I-5 and (B) Hymexazole
(A) compound I-1 and (B) Metconazole, (A) compound I-2 and (B) Metconazole, (A) compound I-3 and (B) Metconazole, (A) compound I-4 and (B) Metconazole, (A) compound I-5 and (B) Metconazole
(A) compound I-1 and (B) Simeconazole, (A) compound I-2 and (B) Simeconazole, (A) compound I-3 and (B) Simeconazole, (A) compound I-4 and (B) Simeconazole, (A) compound I-5 and (B) Simeconazole
(A) compound I-1 and (B) Triflumizole, (A) compound I-2 and (B) Triflumizole, (A) compound I-3 and (B) Triflumizole, (A) compound I-4 and (B) Triflumizole, (A) compound I-5 and (B) Triflumizole
(A) compound I-1 and (B) N-[2-(1,3-Dimethylbutyl)phenyl]-5-fluor-1,3-dimethyl-1H-pyra¬zole-4-carbox¬amide, (A) compound I-2 and (B) N-[2-(1,3-Dimethylbutyl)phenyl]-5-fluor-1,3-dimethyl-1H-pyra¬zole-4-carbox¬amide, (A) compound I-3 and (B) N-[2-(1,3-Dimethylbutyl)phenyl]-5-fluor-1,3-dimethyl-1H-pyra¬zole-4-carbox¬amide, (A) compound I-4 and (B) N-[2-(1,3-Dimethylbutyl)phenyl]-5-fluor-1,3-dimethyl-1H-pyra¬zole-4-carbox¬amide, (A) compound I-5 and (B) N-[2-(1,3-Dimethylbutyl)phenyl]-5-fluor-1,3-dimethyl-1H-pyra¬zole-4-carbox¬amide
(A) compound I-1 and (B) Bixafen, (A) compound I-2 and (B) Bixafen, (A) compound I-3 and (B) Bixafen, (A) compound I-4 and (B) Bixafen, (A) compound I-5 and (B) Bixafen
(A) compound I-1 and (B) Sedexane, (A) compound I-2 and (B) Sedexane, (A) compound I-3 and (B) Sedexane, (A) compound I-4 and (B) Sedexane, (A) compound I-5 and (B) Sedexane
(A) compound I-1 and (B) Fluopyram, (A) compound I-2 and (B) Fluopyram, (A) compound I-3 and (B) Fluopyram, (A) compound I-4 and (B) Fluopyram, (A) compound I-5 and (B) Fluopyram
(A) compound I-1 and (B) Boscalid, (A) compound I-2 and (B) Boscalid, (A) compound I-3 and (B) Boscalid, (A) compound I-4 and (B) Boscalid, (A) compound I-5 and (B) Boscalid
(A) compound I-1 and (B) Carboxin, (A) compound I-2 and (B) Carboxin, (A) compound I-3 and (B) Carboxin, (A) compound I-4 and (B) Carboxin, (A) compound I-5 and (B) Carboxin
(A) compound I-1 and (B) Prochloraz, (A) compound I-2 and (B) Prochloraz, (A) compound I-3 and (B) Prochloraz, (A) compound I-4 and (B) Prochloraz, (A) compound I-5 and (B) Prochloraz
(A) compound I-1 and (B) Carbendazim, (A) compound I-2 and (B) Carbendazim, (A) compound I-3 and (B) Carbendazim, (A) compound I-4 and (B) Carbendazim, (A) compound I-5 and (B) Carbendazim
(A) compound I-1 and (B) Thiram, (A) compound I-2 and (B) Thiram, (A) compound I-3 and (B) Thiram, (A) compound I-4 and (B) Thiram, (A) compound I-5 and (B) Thiram
(A) compound I-1 and (B) Fluopicolide, (A) compound I-2 and (B) Fluopicolide, (A) compound I-3 and (B) Fluopicolide, (A) compound I-4 and (B) Fluopicolide, (A) compound I-5 and (B) Fluopicolide
(A) compound I-1 and (B) Fenamidone, (A) compound I-2 and (B) Fenamidone, (A) compound I-3 and (B) Fenamidone, (A) compound I-4 and (B) Fenamidone, (A) compound I-5 and (B) Fenamidone
(A) compound I-1 and (B) Fludioxinil, (A) compound I-2 and (B) Fludioxinil, (A) compound I-3 and (B) Fludioxinil, (A) compound I-4 and (B) Fludioxinil, (A) compound I-5 and (B) Fludioxinil
(A) compound I-1 and (B) Metalaxyl, (A) compound I-2 and (B) Metalaxyl, (A) compound I-3 and (B) Metalaxyl, (A) compound I-4 and (B) Metalaxyl, (A) compound I-5 and (B) Metalaxyl
(A) compound I-1 and (B) Mefenoxam, (A) compound I-2 and (B) Mefenoxam, (A) compound I-3 and (B) Mefenoxam, (A) compound I-4 and (B) Mefenoxam, (A) compound I-5 and (B) Mefenoxam
(A) compound I-1 and (B) MTF-154 (Mitsui), (A) compound I-2 and (B) MTF-154 (Mitsui), (A) compound I-3 and (B) MTF-154 (Mitsui), (A) compound I-4 and (B) MTF-154 (Mitsui), (A) compound I-5 and (B) MTF-154 (Mitsui)
(A) compound I-1 and (B) Zoxamide, (A) compound I-2 and (B) Zoxamide, (A) compound I-3 and (B) Zoxamide, (A) compound I-4 and (B) Zoxamide, (A) compound I-5 and (B) Zoxamide
(A) compound I-1 and (B) Furametanyl, (A) compound I-2 and (B) Furametanyl, (A) compound I-3 and (B) Furametanyl, (A) compound I-4 and (B) Furametanyl, (A) compound I-5 and (B) Furametanyl
(A) compound I-1 and (B) Tecloftalam, (A) compound I-2 and (B) Tecloftalam, (A) compound I-3 and (B) Tecloftalam, (A) compound I-4 and (B) Tecloftalam, (A) compound I-5 and (B) Tecloftalam
(A) compound I-1 and (B) Oxolinic-acid, (A) compound I-2 and (B) Oxolinic-acid, (A) compound 1-3 and (B) Oxolinic-acid, (A) compound I-4 and (B) Oxolinic-acid, (A) compound I-5 and (B) Oxolinic-acid
(A) compound I-1 and (B) Chlorothalonil, (A) compound I-2 and (B) Chlorothalonil, (A) compound I-3 and (B) Chlorothalonil, (A) compound I-4 and (B) Chlorothalonil, (A) compound I-5 and (B) Chlorothalonil
(A) compound I-1 and (B) Metalaxyl, (A) compound I-2 and (B) Metalaxyl, (A) compound I-3 and (B) Metalaxyl, (A) compound I-4 and (B) Metalaxyl, (A) compound I-5 and (B) Metalaxyl
(A) compound I-1 and (B) Etridiazole, (A) compound I-2 and (B) Etridiazole, (A) compound I-3 and (B) Etridiazole, (A) compound I-4 and (B) Etridiazole, (A) compound I-5 and (B) Etridiazole
(A) compound I-1 and (B) Thiophanate-methyl, (A) compound I-2 and (B) Thiophanate-methyl, (A) compound I-3 and (B) Thiophanate-methyl, (A) compound I-4 and (B) Thiophanate-methyl, (A) compound I-5 and (B) Thiophanate-methyl
(A) compound I-1 and (B) Thiram, (A) compound I-2 and (B) Thiram, (A) compound I-3 and (B) Thiram, (A) compound I-4 and (B) Thiram, (A) compound I-5 and (B) Thiram (A) compound I-1 and (B) Benomyl, (A) compound I-2 and (B) Benomyl, (A) compound I-3 and (B) Benomyl, (A) compound I-4 and (B) Benomyl, (A) compound I-5 and (B) Benomyl (A) compound I-1 and (B) Copper, (A) compound I-2 and (B) Copper, (A) compound I-3 and (B) Copper, (A) compound I-4 and (B) Copper, (A) compound I-5 and (B) Copper (A) compound I-1 and (B) Copper-oxychloride, (A) compound I-2 and (B) Copper-oxychloride, (A) compound I-3 and (B) Copper-oxychloride, (A) compound I-4 and (B) Copper-oxychloride, (A) compound I-5 and (B) Copper-oxychloride (A) compound I-1 and (B) Validamycin, (A) compound I-2 and (B) Validamycin, (A) compound I-3 and (B) Validamycin, (A) compound I-4 and (B) Validamycin, (A) compound I-5 and (B) Validamycin (A) compound I-1 and (B) Ferimzone, (A) compound I-2 and (B) Ferimzone, (A) compound I-3 and (B) Ferimzone, (A) compound I-4 and (B) Ferimzone, (A) compound I-5 and (B) Ferimzone In conjunction with the present invention compounds (A) and (B) are different from each other.

In the combinations according to the invention the compounds A and B are present in a synergistically effective weight ratio of A:B in a range of 100:1 to 1:100, preferably in a weight ratio of 50:1 to 1:50, most preferably in a weight ratio of 20:1 to 1:20. Further ratios of A:B which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present in tautomeric form, such a compound is understood hereinabove and hereinbelow also to include, where applicable, corresponding tautomeric forms, even when these are not specifically mentioned in each case.

Compounds (A) or compounds (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Compounds (A) or compounds (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compounds (A) or the compounds (B) in free form and in the form of their salts, hereinabove and herein below any reference to the free compounds (A) or free compounds (B) or to their salts should be understood as including also the corresponding salts or the free compounds (A) or free compounds (B), respectively, where appropriate and expedient. The equivalent also applies to tautomers of compounds (A) or compounds (B) and to their salts.

According to the invention the expression "combination" stands for the various combinations of compounds (A) and (B), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (A) and (B) is not essential for working the present invention.

The compounds (B) are listed by common names followed by the corresponding CAS-numbers in parenthesis. If no common name was available at the priority date of the application compounds (B) are listed by IUPAC-names followed by the corresponding CAS-numbers in parenthesis.

In a further aspect there is provided a composition comprising a combination according to this invention. Preferably the fungicidal composition comprises an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Colouring agents such as inorganic pigments, for example iron oxide, titanium oxide, ferrocyanblue, and organic pigments such as alizarin, azo and metallophthalocyanine dyes, and trace elements such as iron, manganese, boron, copper, cobalt, molybdenum and zinc salts can be used.

Optionally, other additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compounds, preferably from 10 to 70% by weight.

The combination or composition according to the invention can be used as such, in form of their formulations or as the use forms prepared therefrom, such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

The treatment of plants and plant parts with the active compound combination according to the invention is carried out directly or by action on their environment, habitat or storage area by means of the normal treatment methods, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

These compositions include not only compositions which are ready to be applied to the plant or seed to be treated by means of a suitable device, such as a spraying or dusting device, but also concentrated commercial compositions which must be diluted before application to the crop.

The active compounds within the composition according to the invention have potent microbicide activity and can be employed for controlling undesired micro-organisms, such as fungi or bacteria, in crop protection or in the protection of materials.

Within the composition according to the invention, fungicide compounds can be employed in crop protection for example for controlling *Plasmodiophoromycetes, Oomycetes, Chytridiomycetes, Zygomycetes, Ascomycetes, Basidiomycetes* and *Deuteromycetes*.

Within the composition according to the invention, bactericide compounds can be employed in crop protection for example for controlling *Pseudomonadaceae, Rhizobiaceae, Enterobacteriaceae, Corynebacteriaceae* and *Streptomycetaceae*.

The fungicide composition according to the invention can be used to curatively or preventively control the phytopathogenic fungi of plants or crops. Thus, according to a further aspect of the invention, there is provided a method for curatively or preventively controlling the phytopathogenic fungi of plants or crops comprising the use of a fungicide composition according to the invention by application to the seed, the plant or to the fruit of the plant or to the soil in which the plant is growing or in which it is desired to grow.

The composition of the invention is also suitable for the treatment of seeds. A large part of the damage caused by pests on cultigens occurs by infestation of the seed during storage and after sowing the seed in the ground as well as during and after germination of the plants. This phase is especially critical since the roots and shoots of the growing plant are particularly sensitive and even a small amount of damage can lead to withering of the whole plant.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rye, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The method of treatment according to the invention is used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co-suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an Eleusine EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is describe. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/BY), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034; or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) hybrid insecticidal protein comprising parts from different secreted proteins from *Bacillus thuringiensis* or *Bacillus cereus*, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants b. plants which contain a stress tolerance enhancing transgene capable of reducing the expression and/or the activity of the PARG encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Examples of plants with the above-mentioned traits are non-exhaustively listed in Table A.

TABLE A

| No. | Effected target or expressed principle(s) | Crop phenotype/Tolerance to |
|---|---|---|
| A-1 | Acetolactate synthase (ALS) | Sulfonylureas, Imidazolinones, Triazolopyrimidines, Pyrimidyloxybenzoates, Phtalides |
| A-2 | AcetylCoA Carboxylase (ACCase) | Aryloxyphenoxyalkanecarboxylic acids, cyclohexanediones |
| A-3 | Hydroxyphenylpyruvate dioxygenase (HPPD) | Isoxazoles such as Isoxaflutol or Isoxachlortol, Triones such as mesotrione or sulcotrione |
| A-4 | Phosphinothricin acetyltransferase | Phosphinothricin |
| A-5 | O-Methyl transferase | altered lignin levels |
| A-6 | Glutamine synthetase | Glufosinate, Bialaphos |
| A-7 | Adenylosuccinate Lyase (ADSL) | Inhibitors of IMP and AMP synthesis |
| A-8 | Adenylosuccinate Synthase | Inhibitors of adenylosuccinate synthesis |
| A-9 | Anthranilate Synthase | Inhibitors of tryptophan synthesis and catabolism |
| A-10 | Nitrilase | 3,5-dihalo-4-hydroxy-benzonitriles such as Bromoxynil and Ioxinyl |
| A-11 | 5-Enolpyruvyl-3phosphoshikimate Synthase (EPSPS) | Glyphosate or sulfosate |
| A-12 | Glyphosate oxidoreductase | Glyphosate or sulfosate |

TABLE A-continued

| No. | Effected target or expressed principle(s) | Crop phenotype/Tolerance to |
|---|---|---|
| A-13 | Protoporphyrinogen oxidase (PROTOX) | Diphenylethers, cyclic imides, phenylpyrazoles, pyridin derivatives, phenopylate, oxadiazoles, etc. |
| A-14 | Cytochrome P450 eg. P450 SU1 | Xenobiotics and herbicides such as Sulfonylureas |
| A-15 | Dimboa biosynthesis (Bxl gene) | *Helminthosporium turcicum*, *Rhopalosiphum maydis*, *Diplodia maydis*, *Ostrinia nubilalis*, *lepidoptera* sp. |
| A-16 | CMIII (small basic maize seed peptide) | plant pathogenes eg. *fusarium, alternaria, sclerotina* |
| A-17 | Corn-SAFP (zeamatin) | plant pathogenes eg. *fusarium, alternaria, sclerotina, rhizoctonia, chaetomium, phycomyces* |
| A-18 | Hml gene | *Cochliobulus* |
| A-19 | Chitinases | plant pathogenes |
| A-20 | Glucanases | plant pathogenes |
| A-21 | Coat proteins | viruses such as maize dwarf mosaic virus, maize chlorotic dwarf virus |
| A-22 | *Bacillus thuringiensis* toxins, VIP 3, *Bacillus cereus* toxins, *Photorabdus* and *Xenorhabdus* toxins | *lepidoptera, coleoptera, diptera*, nematodes, eg. *ostrinia nubilalis, heliothis zea*, armyworms eg. *Spodoptera frugiperda*, corn rootworms, *sesamia* sp., black cutworm, asian corn borer, weevils |
| A-23 | 3-Hydroxysteroid oxidase | *lepidoptera, coleoptera, diptera*, nematodes, eg. *ostrinia nubilalis, heliothis zea*, armyworms eg. *Spodoptera frugiperda*, corn rootworms, *sesamia* sp., black cutworm, asian corn borer, weevils |
| A-24 | Peroxidase | *lepidoptera, coleoptera, diptera*, nematodes, eg. *ostrinia nubilalis, heliothis zea*, armyworms eg. *spodoptera frugiperda*, corn rootworms, *sesamia* sp., black cutworm, asian corn borer, weevils |
| A-25 | Aminopeptidase inhibitors eg. Leucine aminopeptidase inhibitor (LAPI) | *lepidoptera, coleoptera, diptera*, nematodes, eg. *ostrinia nubilalis, heliothis zea*, armyworms eg. *spodoptera frugiperda*, corn rootworms, *sesamia* sp., black cutworm, asian corn borer, weevils |
| A-26 | Limonene synthase | corn rootworms |
| A-27 | Lectines | *lepidoptera, coleoptera, diptera*, nematodes, eg. *ostrinia nubilalis, heliothis zea*, armyworms eg. *spodoptera frugiperda*, corn rootworms, *sesamia* sp., black cutworm, asian corn borer, weevils |
| A-28 | Protease Inhibitors eg. cystatin, patatin, virgiferin, CPTI | weevils, corn rootworm |
| A-29 | ribosome inactivating protein | *lepidoptera, coleoptera, diptera*, nematodes, eg. *ostrinia nubilalis, heliothis zea*, armyworms eg. *spodoptera frugiperda*, corn rootworms, *sesamia* sp., black cutworm, asian corn borer, weevils |
| A-30 | maize 5C9 polypeptide | *lepidoptera, coleoptera, diptera*, nematodes, eg. *ostrinia nubilalis, heliothis zea*, armyworms eg. *spodoptera frugiperda*, corn rootworms, *sesamia* sp., black cutworm, asian corn borer, weevils |
| A-31 | HMG-CoA reductase | *lepidoptera, coleoptera, diptera*, nematodes, eg. *ostrinia nubilalis, heliothis zea*, armyworms eg. *spodoptera frugiperda*, corn rootworms, *sesamia* sp., black cutworm, asian corn borer, weevils |
| A-32 | Inhibition of protein synthesis | Chloroactanilides such as Alachlor, Acetochlor, Dimethenamid |
| A-33 | Hormone mimic | 2,4-D, Mecoprop-P |

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan, 3) transgenic plants which produce hyaluronan.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

A further aspect of the instant invention is a method of protecting natural substances of vegetable or animal origin or their processed forms, which have been taken from the natural life cycle, which comprises applying to said natural substances of vegetable or animal origin or their processed forms a combination of compounds (A) and (B) in a synergistically effective amount.

A preferred embodiment is a method of protecting natural substances of vegetable origin or their processed forms, which have been taken from the natural life cycle, which comprises applying to said natural substances of vegetable origin or their processed forms a combination of compounds (A) and (B) in a synergistically effective amount.

A further preferred embodiment is a method of protecting fruit, preferably pomes, stone fruits, soft fruits and citrus fruits, or their processed forms, which have been taken from the natural life cycle, which comprises applying to said natural substances of vegetable origin or their processed forms a combination of compounds (A) and (B) in a synergistically effective amount.

The combinations of the present invention may also be used in the field of protecting technical material against attack of fungi. According to the instant invention, the term "technical material" includes paper; carpets; constructions; cooling and heating systems; wall-boards; ventilation and air conditioning systems and the like. The combinations according the present invention can prevent disadvantageous effects such as decay, discoloration or mold. Preferably "storage goods" is understood to denote wall-boards.

The method of treatment according to the invention can also be used in the field of protecting storage goods against attack of fungi. According to the instant invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

In another preferred embodiment of the invention "storage goods" is understood to denote wood. The fungicide combination or composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

Among the diseases of plants or crops that can be controlled by the method according to the invention, mention may be made of:

Powdery Mildew Diseases such as
Blumeria diseases caused for example by *Blumeria graminis*
Podosphaera diseases caused for example by *Podosphaera leucotricha*
Sphaerotheca diseases caused for example by *Sphaerotheca fuliginea*
Uncinula diseases caused for example by *Uncinula necator*
Rust Diseases such as
Gymnosporangium diseases caused for example by *Gymnosporangium sabinae*
Hemileia diseases caused for example by *Hemileia vastatrix*
Phakopsora diseases caused for example by *Phakopsora pachyrhizi* and *Phakopsora meibomiae*
Puccinia diseases caused for example by *Puccinia recondite*, and *Puccinia triticina*;
Uromyces diseases caused for example by *Uromyces appendiculatus*
Oomycete Diseases such as
Bremia diseases caused for example by *Bremia lactucae*
Peronospora diseases caused for example by *Peronospora pisi* and *Peronospora brassicae*
Phytophthora diseases caused for example by *Phytophthora infestans*
Plasmopara diseases caused for example by *Plasmopara viticola*
Pseudoperonospora diseases caused for example by *Pseudoperonospora humuli* and *Pseudoperonospora cubensis*
Pythium diseases caused for example by *Pythium ultimum*
Leafspot, Leaf blotch and Leaf Blight Diseases such as
Alternaria diseases caused for example by *Alternaria solani*
Cercospora diseases caused for example by *Cercospora beticola*
Cladiosporium diseases caused for example by *Cladiosporium cucumerinum*
Cochliobolus diseases caused for example by *Cochliobolus sativus* (Conidiaform: *Drechslera*, Syn: *Helminthosporium*);
Colletotrichum diseases caused for example by *Colletotrichum lindemuthianum*
Cycloconium diseases caused for example by *Cycloconium oleaginum*
Diaporthe diseases caused for example by *Diaporthe citri*
Elsinoe diseases caused for example by *Elsinoe fawcettii*
Gloeosporium diseases caused for example by *Gloeosporium laeticolor*
Glomerella diseases caused for example by *Glomerella cingulata*
Guignardia diseases caused for example by *Guignardia bidwellii*
Leptosphaeria diseases caused for example by *Leptosphaeria maculans*
Magnaporthe diseases caused for example by *Magnaporthe grisea*
Mycosphaerella diseases caused for example by *Mycosphaerella graminicola* and *Mycosphaerella fijiensis*
Phaeosphaeria diseases caused for example by *Phaeosphaeria nodorum*
Pyrenophora diseases caused for example by *Pyrenophora teres*

*Ramularia* diseases caused for example by *Ramularia collo-cygni*

*Rhynchosporium* diseases caused for example by *Rhynchosporium secalis*

*Septoria* diseases caused for example by *Septoria apii;*

*Typhula* diseases caused for example by *Thyphula incarnata*

*Venturia* diseases caused for example by *Venturia inaequalis*

Root- and Stem Diseases such as

*Corticium* diseases caused for example by *Corticium graminearum*

*Fusarium* diseases caused for example by *Fusarium oxysporum*

*Gaeumannomyces* diseases caused for example by *Gaeumannomyces graminis*

*Rhizoctonia* diseases caused for example by *Rhizoctonia solani*

*Oculimacula* (*Tapesia*) diseases caused for example by *Oculimacula Tapesia acuformis*

*Thielaviopsis* diseases caused for example by *Thielaviopsis basicola*

Ear and Panicle Diseases including Maize cob such as

*Alternaria* diseases caused for example by *Alternaria* spp.

*Aspergillus* diseases caused for example by *Aspergillus flavus*

*Cladosporium* diseases caused for example by *Cladiosporium cladosporioides*

*Claviceps* diseases caused for example by *Claviceps purpurea*

*Fusarium* diseases caused for example by *Fusarium culmorum*

*Gibberella* diseases caused for example by *Gibberella zeae*

*Monographella* diseases caused for example by *Monographella nivalis*

Smut- and Bunt Diseases such as

*Sphacelotheca* diseases caused for example by *Sphacelotheca reiliana*

*Tilletia* diseases caused for example by *Tilletia caries*

*Urocystis* diseases *Urocystis occulta*

*Ustilago* diseases caused for example by *Ustilago nuda;*

Fruit Rot and Mould Diseases such as

*Aspergillus* diseases caused for example by *Aspergillus flavus*

*Botrytis* diseases caused for example by *Botrytis cinerea*

*Penicillium* diseases caused for example by *Penicillium expansum* and *Penicillium purpurogenum*

*Sclerotinia* diseases caused for example by *Sclerotinia sclerotiorum;*

*Verticillium* diseases caused for example by *Verticillium alboatrum*

Seed- and Soilborne Decay, Mould, Wilt, Rot and Damping-off diseases

*Fusarium* diseases caused for example by *Fusarium culmorum*

*Phytophthora* diseases caused for example by *Phytophthora cactorum*

*Pythium* diseases caused for example by *Pythium ultimum*

*Rhizoctonia* diseases caused for example by *Rhizoctonia solani*

*Sclerotium* diseases caused for example by *Sclerotium rolfsii*

Canker, Broom and Dieback Diseases such as

*Nectria* diseases caused for example by *Nectria galligena*

Blight Diseases such as

*Monilinia* diseases caused for example by *Monilinia laxa*

Leaf Blister or Leaf Curl Diseases including deformation of blooms and fruits such as

*Taphrina* diseases caused for example by *Taphrina deformans*

Decline Diseases of Wooden Plants such as

*Esca* disease caused for example by *Phaeomoniella clamydospora* and *Phaeoacremonium aleophilum* and *Fomitiporia mediterranea*

Diseases of Flowers and Seeds such as

*Botrytis* diseases caused for example by *Botrytis cinerea*

Diseases of Tubers such as

*Rhizoctonia* diseases caused for example by *Rhizoctonia solani*

*Helminthosporium* diseases caused for example by *Helminthosporium solani*

Diseases caused by Bacterial Organisms such as

*Xanthomanas* species for example *Xanthomonas campestris* pv. *Oryzae*

*Pseudomonas* species for example *Pseudomonas syringae* pv. *Lachrymans*

*Erwinia* species for example *Erwinia amylovora.*

The compounds releated to this invention are preferably used to control the following soybean diseases:

Fungal Diseases of the Foliage, Upper Stems, Pods and Seeds for example

*Alternaria* leaf spot (*Alternaria* spec. *atrans tenuissima*), Anthracnose (*Colletotrichum gloeosporoides dematium* var. *truncatum*), Brown spot (*Septoria glycines*), *Cercospora* leaf spot and blight (*Cercospora kikuchii*), *Choanephora* leaf blight (*Choanephora infundibulifera trispora* (Syn.)), *Dactuliophora* leaf spot (*Dactuliophora glycines*), Downy Mildew (*Peronospora manshurica*), *Drechslera* blight (*Drechslera glycini*), Frogeye Leaf spot (*Cercospora sojina*), *Leptosphaerulina* Leaf Spot (*Leptosphaerulina trifolii*), *Phyllosticta* Leaf Spot (*Phyllosticta sojaecola*), Pod and Stem Blight (*Phomopsis sojae*), Powdery Mildew (*Microsphaera diffusa*), *Pyrenochaeta* Leaf Spot (*Pyrenochaeta glycines*), *Rhizoctonia* Aerial, Foliage, and Web Blight (*Rhizoctonia solani*), Rust (*Phakopsora pachyrhizi, Phakopsora meibomiae*), Scab (*Sphaceloma glycines*), *Stemphylium* Leaf Blight (*Stemphylium botryosum*), Target Spot (*Corynespora cassiicola*)

Fungal Disease of the Roots and Lower Stems for example

Black Root Rot (*Calonectria crotalariae*), Charcoal Rot (*Macrophomina phaseolina*), *Fusarium* Blight or Wilt, Root Rot, and Pod and Collar Rot (*Fusarium oxysporum, Fusarium orthoceras, Fusarium semitectum, Fusarium equiseti*), *Mycoleptodiscus* Root Rot (*Mycoleptodiscus terrestris*), *Neocosmospora* (*Neocosmopspora vasinfecta*), Pod and Stem Blight (*Diaporthe phaseolorum*), Stem Canker (*Diaporthe phaseolorum* var. *caulivora*), *Phytophthora* Rot (*Phytophthora megasperma*), Brown Stem Rot (*Phialophora gregata*), *Pythium* Rot (*Pythium aphanidermatum, Pythium irregulare, Pythium debaryanum, Pythium myriotylum, Pythium ultimum*), *Rhizoctonia* Root Rot, Stem Decay, and Damping-Off (*Rhizoctonia solani*), *Sclerotinia* Stem Decay (*Sclerotinia sclerotiorum*), *Sclerotinia* Southern Blight (*Sclerotinia rolfsii*), *Thielaviopsis* Root Rot (*Thielaviopsis basicola*).

The method of treatment according to the invention also provides the use of compounds (A) and (B) in a simultaneous, separate or sequential manner.

The dose of active compound usually applied in the method of treatment according to the invention is generally and advantageously for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 0.1 to 200 g per 100 kilogram of seed, preferably from 0.2 to 150 g per 100 kilogram of seed, most preferably from 0.5 to 100 g per 100 kilogram of seed;

for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The compounds or mixtures according to the invention may also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

Mycotoxins

Furthermore compounds or mixtures according to the invention may also be used to reduce the contents of mycotoxins in the harvested crops and therefore in foods and animal feed stuff made therefrom.

Especially but not exclusively the following mycotoxins can be specified:

Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalcaloides und Aflatoxins, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

Treatment of Seeds

The invention comprises a procedure in which the seed is treated at the same time with a compound of Group (A) and a compound selected from group (B). It further comprises a method in which the seed is treated with compound of Group (A) and a compound selected from group (B) separately.

The invention also comprises a seed, which has been treated with a compound of Group (A) and a compound selected from group (B) at the same time. The invention also comprises a seed, which has been treated with a compound of Group (A) and a compound selected from group (B) separately. For the latter seed, the active ingredients can be applied in separate layers. These layers can optionally be separated by an additional layer that may or may not contain an active ingredient.

The mixtures of the invention are particularly suitable for the treatment of seeds. A large part of the damage caused by pests on cultigens occurs by infestation of the seed during storage and after sowing the seed in the ground as well as during and after germination of the plants. This phase is especially critical since the roots and shoots of the growing plant are particularly sensitive and even a small amount of damage can lead to withering of the whole plant. There is therefore considerable interest in protecting the seed and the germinating plant by the use of suitable agents.

The control of pests by treatment of the seeds of plants has been known for a considerable time and is the object of continuous improvement. However, there are a number of problems in the treatment of seed that cannot always be satisfactorily solved. Therefore it is worthwhile to develop methods for the protection of seeds and germinating plants which makes the additional application of plant protection agents after seeding or after germination of the plants superfluous. It is further worthwhile to optimize the amount of the applied active material such that the seed and the germinating plants are protected against infestation by pests as best as possible without the plants themselves being damaged by the active compound applied. In particular, methods for the treatment seed should also take into account the intrinsic fungicidal properties of transgenic plants in order to achieve optimal protection of the seed and germinating plants with a minimal expenditure of plant protection agents.

The present invention relates therefore especially to a method for the protection of seed and germinating plants from infestation with pests in that the seed is treated with the combination/composition of the invention. In addition the invention relates also to the use of the combination/composition of the invention for the treatment seed for protection of the seed and the germinating plants from pests. Furthermore the invention relates to seed which was treated with an combination/composition of the invention for protection from pests.

One of the advantages of the invention is because of the special systemic properties of the combination/composition of the invention treatment with these combination/composition protects not only the seed itself from pests but also the plants emerging after sprouting. In this way the direct treatment of the culture at the time of sowing or shortly thereafter can be omitted.

A further advantage is the synergistic increase in fungicidal activity of the combination/composition of the invention in comparison to the respective individual active compounds, which extends beyond the sum of the activity of both individually applied active compounds. In this way an optimization of the amount of active compound applied is made possible.

It is also be regarded as advantageous that the mixtures of the invention can also be used in particular with transgenic seeds whereby the plants emerging from this seed are capable of the expression of a protein directed against pests. By treatment of such seed with the agents of the invention certain pests can already be controlled by expression of the, for example, fungicidal protein, and it is additionally surprising that a synergistic activity supplementation occurs with the agents of the invention, which improves still further the effectiveness of the protection from pest infestation.

The agents of the invention are suitable for the protection of seed of plant varieties of all types as already described which are used in agriculture, in greenhouses, in forestry, in garden construction or in vineyards. In particular, this concerns seed of maize, peanut, canola, rape, poppy, olive, coconut, cacao, soy, cotton, beet, (e.g. sugar beet and feed beet), rice, millet, wheat, barley, oats, rye, sunflower, sugar cane or tobacco. The combination/compositions of the invention are also suitable for the treatment of the seed of fruit plants and vegetables as previously described. Particular importance is attached to the treatment of the seed of maize, soy, cotton, wheat and canola or rape.

As already described, the treatment of transgenic seed with a combination/composition of the invention is of particular importance. This concerns the seeds of plants which generally contain at least one heterologous gene that controls the expression of a polypeptide with special fungicidal properties. The heterologous gene in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed that contains at least one heterologous gene that originates from *Bacillus* sp. and whose gene product exhibits activity against the European corn borer and/or western corn rootworm. Particularly preferred is a heterologous gene that originates from *Bacillus thuringiensis*.

Within the context of the present invention the combination/composition of the invention is applied to the seed alone or in a suitable formulation. Preferably the seed is handled in a state in which it is so stable, that no damage occurs during treatment. In general treatment of the seed can be carried out at any time between harvest and sowing. Normally seed is used that was separated from the plant and has been freed of spadix, husks, stalks, pods, wool or fruit flesh. Use of seed that was harvested, purified, and dried to moisture content of below 15% w/w. Alternatively, seed treated with water after drying and then dried again can also be used.

In general care must be taken during the treatment of the seed that the amount of the combination/composition of the invention and/or further additive applied to the seed is so chosen that the germination of the seed is not impaired and the emerging plant is not damaged. This is to be noted above all with active compounds which can show phytotoxic effects when applied in certain amounts.

The combination/compositions of the invention can be applied directly, that is without containing additional components and without being diluted. It is normally preferred to apply the combination/composition to the seed in the form of a suitable formulation. Suitable formulations and methods for seed treatment are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

According to another aspect of the present invention, in the combination or composition according to the invention, the compound ratio A/B may be advantageously chosen so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = X + Y - \frac{XY}{100}$$

wherein E represents the expected percentage of inhibition of the pest for the combination of the two compounds at defined doses (for example equal to x and y respectively), X is the percentage of inhibition observed for the pest by compound (A) at a defined dose (equal to x), Y is the percentage of inhibition observed for the pest by compound (B) at a defined dose (equal to y). When the percentage of inhibition observed for the combination is greater than E, there is a synergistic effect.

The term "synergistic effect" also means the effect defined by application of the Tammes method, "Isoboles, a graphic representation of synergism in pesticides", Netherlands Journal of Plant Pathology, 70(1964), pages 73-80.

A synergistic effect in fungicides is always present when the fungicidal action of the active compound combinations exceeds the expected action of the active compounds.

The expected fungicidal action for a given combination of two or three active compounds can be calculated as follows, according to S. R. Colby ("Calculating Synergistic and Antagonistic Responses of Herbicide Combinations", Weeds 1961 15, 20-22):

If

X is the efficacy when employing active compound A at an application rate of m g/ha, Y is the efficacy when employing active compound B at an application rate of n g/ha and E is the efficacy when employing active compounds A and B at application rates of m and n g/ha, then $$E = X + Y - \frac{X \cdot N}{100}.$$

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

The invention is illustrated by the examples below. However, the invention is not limited to the examples.

EXAMPLE

*Pyrenophora teres*-Test (Barley)/Preventive

Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried on, the plants are sprayed with a spore suspension of *Pyrenophora teres*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present.

TABLE

*Pyrenophora teres*-test (barley)/preventive

| Active compound Known: | Rate of application of active compound in ppm | Efficacy in % |
|---|---|---|
| Ex I-2 | 250 | 0 |

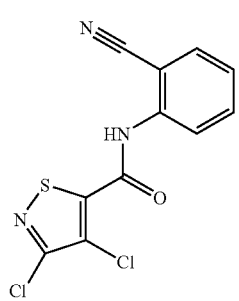 [SMILES: N#Cc1ccccc1NC(=O)c1snc(Cl)c1Cl]

TABLE-continued

*Pyrenophora teres*-test (barley)/preventive

| Active compound Known: | Rate of application of active compound in ppm | Efficacy in % |
|---|---|---|
| Ex B3 Bixafen | 62.5 | 78 |

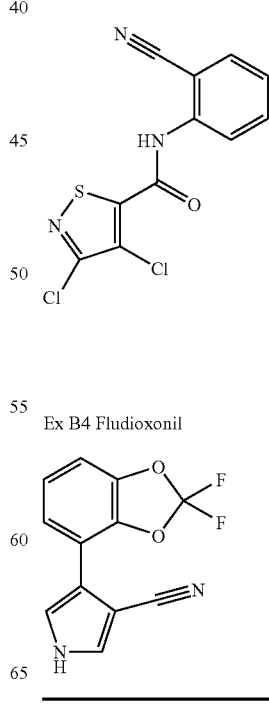

Inventive Compound Combination:

| | Ratio of the mixture | Rate of application of active compound in ppm | Actual efficacy | Expected value, calculated using Colby's formula |
|---|---|---|---|---|
| Ex I-2 + Ex B3 Bixafen | 4:1 | 250 + 62.5 | 100 | 78 |

TABLE

*Pyrenophora teres*-test(barley)/preventive

| Active compound Known: | Rate of application of active compound in ppm | Efficacy in % |
|---|---|---|
| Ex I-2 | 1000 | 11 |
| Ex B4 Fludioxonil | 125 | 44 |

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Fludioxonil | 8:1 | 1000 + 125 | 100 | 50 |

TABLE

*Pyrenophora teres*-test (barley)/preventive

| Active compound Known: | Rate of application of active compound in ppm | Efficacy in % |
|---|---|---|
| Ex I-2 | 1000 | 11 |

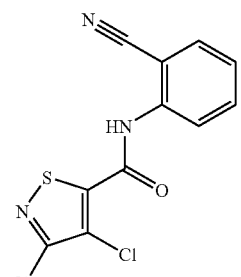

| Ex B1 Fluoxastrobin | 62.5 | 67 |

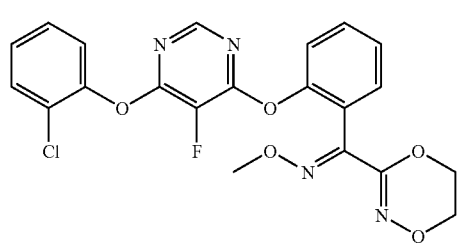

Inventive Compound Combination:

| | Ratio of the mixture | Rate of application of active compound in ppm | Actual efficacy | Expected value, calculated using Colby's formula |
|---|---|---|---|---|
| Ex I-2 + Ex B1 Fluoxastrobin | 16:1 | 1000 + 62.5 | 100 | 71 |

TABLE

*Pyrenophora teres*-test (barley)/preventive

| Active compound Known: | Rate of application of active compound in ppm | Efficacy in % |
|---|---|---|
| Ex I-2 | 1000 | 11 |

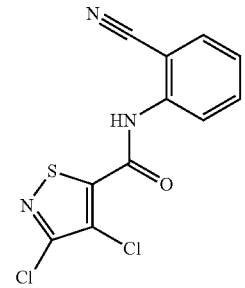 [SMILES: N#Cc1ccccc1NC(=O)c1snc(Cl)c1Cl]

TABLE-continued

*Pyrenophora teres*-test (barley)/preventive

| Active compound Known: | Rate of application of active compound in ppm | Efficacy in % |
|---|---|---|
| Ex B2 Hymexazol | 1000 | 0 |

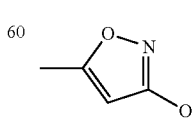

Inventive Compound Combination:

| | Ratio of the mixture | Rate of application of active compound in ppm | Actual efficacy | Expected value, calculated using Colby's formula |
|---|---|---|---|---|
| Ex I-2 + Ex B2 Hymexazol | 1:1 | 1000 + 1000 | 78 | 11 |

TABLE

Pyrenophora teres-test (barley)/preventive

| Active compound Known: | Rate of application of active compound in ppm | Efficacy in % |
|---|---|---|
| Ex I-2 | 1000 | 11 |

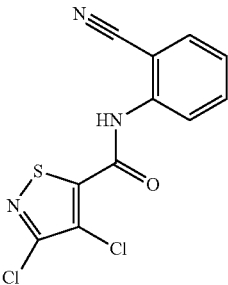

| Ex B2 Ipconazole | 250 | 33 |

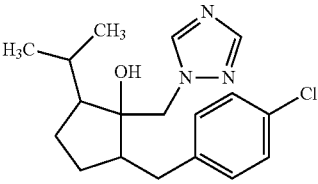 [SMILES: CC(C)C1CCC(Cc2ccc(Cl)cc2)C1(O)Cn1cncn1]

Inventive Compound Combination:

| | Ratio of the mixture | Rate of application of active compound in ppm | Actual efficacy | Expected value, calculated using Colby's formula |
|---|---|---|---|---|
| Ex I-2 + Ex B2 Ipconazole | 4:1 | 1000 + 250 | 89 | 40 |

TABLE

Pyrenophora teres-test (barley)/preventive

| Active compound Known: | Rate of application of active compound in ppm | Efficacy in % |
|---|---|---|
| Ex I-2 | 250 | 0 |
| Ex B3 N-[2-(1,3-Dimethylbutyl)phenyl]-5-fluor-1,3-dimethyl-1H-pyrazole-4-carboxamide | 62.5 | 89 |

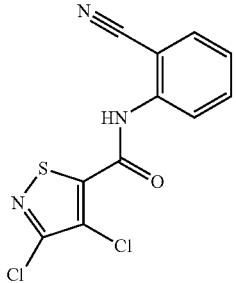 [SMILES: N#Cc1ccccc1NC(=O)c1snc(Cl)c1Cl]

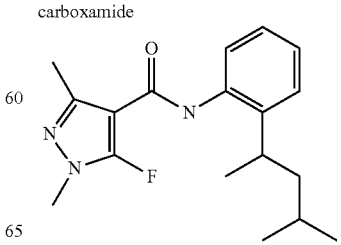

Inventive Compound Combination:

| | Ratio of the mixture | Rate of application of active compound in ppm | Actual efficacy | Expected value, calculated using Colby's formula |
|---|---|---|---|---|
| Ex I-2 + Ex B3 N-[2-(1,3-Dimethylbutyl)phenyl]-5-fluor-1,3-dimethyl-1H-pyrazole-4-carboxamide | 4:1 | 250 + 62.5 | 100 | 89 |

TABLE

*Pyrenophora teres*-test (barley)/preventive

| Active compound Known: | Rate of application of active compound in ppm | Efficacy in % |
|---|---|---|
| Ex I-2 | 250 | 0 |
| Ex B4 Prochloraz | 62.5 | 89 |

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Prochloraz | 4:1 | 250 + 62.5 | 100 | 89 |

Example

Septoria tritici-Test (Wheat)/Preventive

Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried on, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present.

TABLE

| Septoria tritici-test (wheat)/preventive | | |
|---|---|---|
| Active compound Known: | Rate of application of active compound in ppm | Efficacy in % |
| Ex I-2 | 1000 | 0 |

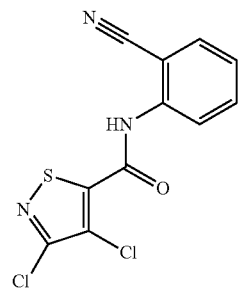 [SMILES: N#Cc1ccccc1NC(=O)c1snc(Cl)c1Cl]

TABLE-continued

| Septoria tritici-test (wheat)/preventive | | |
|---|---|---|
| Active compound Known: | Rate of application of active compound in ppm | Efficacy in % |
| Ex B4 Metalaxyl | 1000 | 33 |

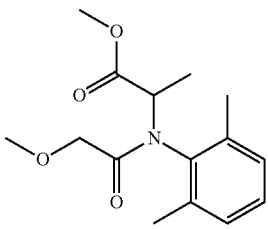 [SMILES: COCC(=O)N(c1c(C)cccc1C)C(C)C(=O)OC]

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Metalaxyl | 1:1 | 1000 + 1000 | 67 | 33 |

TABLE

| Septoria tritici-test (wheat)/preventive | | |
|---|---|---|
| Active compound Known: | Rate of application of active compound in ppm | Efficacy in % |
| Ex I-2 | 1000 | 0 |

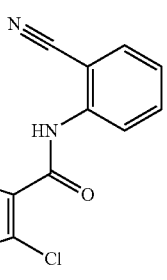

| Ex B2 Simeconazole | 1000 | 67 |

Inventive Compound Combination:

| | Ratio of the mixture | Rate of application of active compound in ppm | Actual efficacy | Expected value, calculated using Colby's formula |
|---|---|---|---|---|
| Ex I-2 + Ex B2 Simeconazole | } 1:1 | 1000 + 1000 } | 94 | 67 |

TABLE

Septoria tritici-test (wheat)/preventive

| Active compound Known: | Rate of application of active compound in ppm | Efficacy in % |
|---|---|---|
| Ex I-2 | 1000 | 0 |
| Ex B1 Trifloxystrobin | 62.5 | 94 |

Inventive Compound Combination:

| | Ratio of the mixture | Rate of application of active compound in ppm | Actual efficacy | Expected value, calculated using Colby's formula |
|---|---|---|---|---|
| Ex I-2 + Ex B1 Trifloxystrobin | } 16:1 | 1000 + 62.5 } | 100 | 94 |

Example

Blumeria Test (Wheat)/Preventive

Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried on, the plants are dusted with spores of Blumeria graminis f.sp. tritici.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present

TABLE

*Blumeria* test (wheat)/preventive

| Active compound Known: | Rate of application of active compound in ppm | Efficacy in % |
|---|---|---|
| Ex I-2 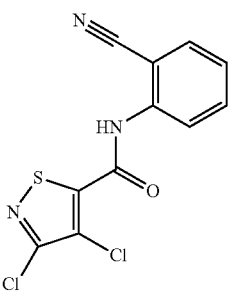 [SMILES: N#Cc1ccccc1NC(=O)c1snc(Cl)c1Cl] | 1000 | 22 |
| Ex B4 Metalaxyl M 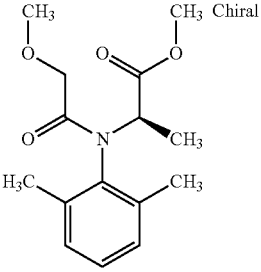 | 250 | 0 |

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Metalaxyl M | 4:1 | 1000 + 250 | 89 | 22 |

Example

*Sphaerotheca* Test (Cucumbers)/Protective

Solvent: 24,5 parts by weight of acetone
24,5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protect activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present.

Example

*Sphaerotheca* test (cucumbers)/protective

| Active compound Known: | Rate of application of active compound in ppm | Efficacy in % |
|---|---|---|
| Ex I-2 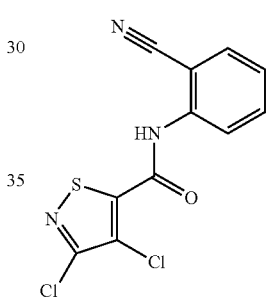 | 100 | 0 |
| | 50 | 0 |

-continued

*Sphaerotheca* test (cucumbers)/protective

| Active compound Known: | Rate of application of active compound in ppm | Efficacy in % |
|---|---|---|
| Ex B2 Ipconazole 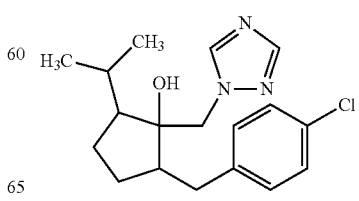 | 10 | 77 |
| | 5 | 50 |

Inventive Compound Combination:

| | Ratio of the mixture | Rate of application of active compound in ppm | Actual efficacy | Expected value, calculated using Colby's formula |
|---|---|---|---|---|
| Ex I-2 + Ex B2 Ipconazole | 10:1 | 100 + 10 | 97 | 77 |
| Ex I-2 + Ex B2 Ipconazole | 10:1 | 50 + 5 | 78 | 50 |

Example

*Venturia* Test (Apples)/Protective

Solvent: 24,5 parts by weight of acetone 24,5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present Example

*Venturia* test (apples)/protective

| Active compound Known: | Rate of application of active compound in ppm | Efficacy in % |
|---|---|---|
| Ex I-2 | 100 | 19 |
| | 50 | 0 |

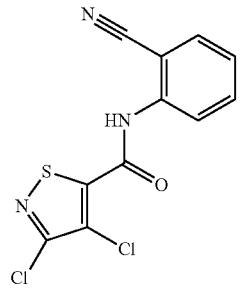 [SMILES: N#Cc1ccccc1NC(=O)c1snc(Cl)c1Cl]

| Ex B4 Fludioxonil | 100 | 30 |
| | 50 | 26 |

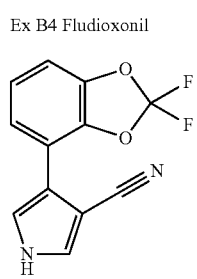

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Fludioxonil | 1:1 | 100 + 100 | 91 | 43 |
| Ex I-2 + Ex B4 Fludioxonil | 1:1 | 50 + 50 | 66 | 26 |

Example 43

Venturia test (apples)/protective

| Active compound Known: | Rate of application of active compound in ppm | Efficacy in % |
|---|---|---|
| Ex I-2 | 200 | 37 |

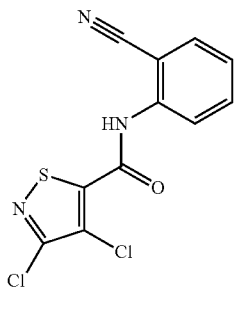 [SMILES: N#Cc1ccccc1NC(=O)c1snc(Cl)c1Cl]

| | | |
|---|---|---|
| Ex B4 Metalaxyl M | 200 | 29 |

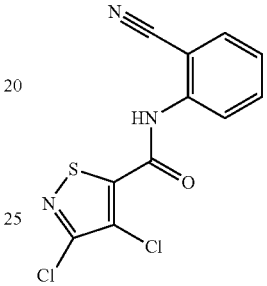

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Metalaxyl M | 1:1 | 200 + 200 | 74 | 55 |

Example 44

Venturia test (apples)/protective

| Active compound Known: | Rate of application of active compound in ppm | Efficacy in % |
|---|---|---|
| Ex I-2 | 100 | 19 |

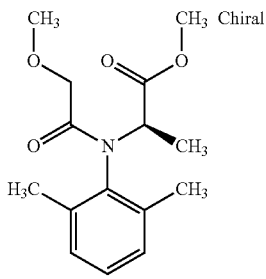

| | | |
|---|---|---|
| Ex B3 Bixafen | 1 | 73 |

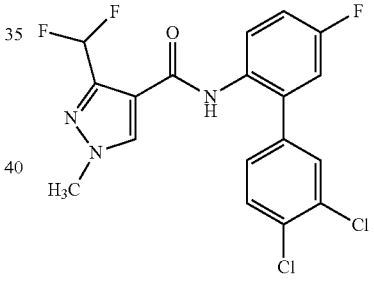

Inventive Compound Combination:

| | Ratio of the mixture | Rate of application of active compound in ppm | Actual efficacy | Expected value, calculated using Colby's formula |
|---|---|---|---|---|
| Ex I-2 + Ex B3 Bixafen | 100:1 | 100 + 1 | 97 | 78 |

Example

*Uromyces* Test (Beans)/Protective

Solvent: 24,5 parts by weight of acetone
24,5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present.

Example

*Uromyces* test (beans)/protective

| Active compound Known: | Rate of application of active compound in ppm | Efficacy in % |
|---|---|---|
| Ex I-2 | 100 | 0 |

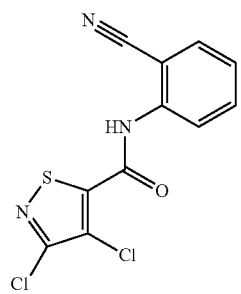 [SMILES: N#Cc1ccccc1NC(=O)c1snc(Cl)c1Cl]

| Ex B1 Trifloxystrobin | 1 | 70 |

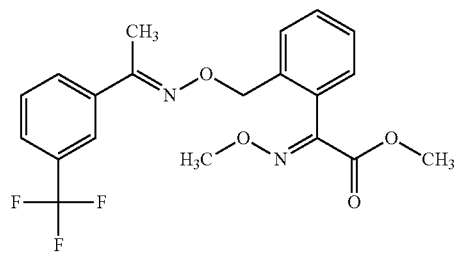 [SMILES: CO/N=C(/C(=O)OC)c1ccccc1CO/N=C(\C)c1cccc(C(F)(F)F)c1]

Inventive Compound Combination:

| | Ratio of the mixture | Rate of application of active compound in ppm | Actual efficacy | Expected value, calculated using Colby's formula |
|---|---|---|---|---|
| Ex I-2 + Ex B1 Trifloxystrobin | 100:1 | 100 + 1 | 95 | 70 |

Example 47

Uromyces test (beans)/protective

| Active compound Known: | Rate of application of active compound in ppm | Efficacy in % |
|---|---|---|
| Ex I-2 | 50 | 8 |

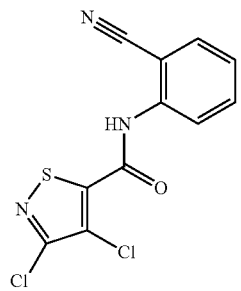 [SMILES: N#Cc1ccccc1NC(=O)c1snc(Cl)c1Cl]

| | | |
|---|---|---|
| Ex B2 Simeconazole | 5 | 84 |

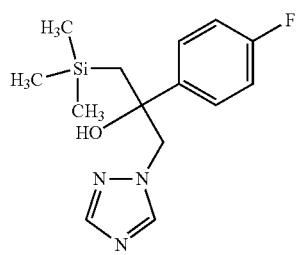 [SMILES: C[Si](C)(C)CC(O)(Cn1cncn1)c1ccc(F)cc1]

Inventive Compound Combination:

| | Ratio of the mixture | Rate of application of active compound in ppm | Actual efficacy | Expected value, calculated using Colby's formula |
|---|---|---|---|---|
| Ex I-2 + Ex B2 Simeconazole | 10:1 | 50 + 5 | 96 | 85 |

Example 48

Uromyces test (beans)/protective

| Active compound Known: | Rate of application of active compound in ppm | Efficacy in % |
|---|---|---|
| Ex I-2 | 200 | 15 |

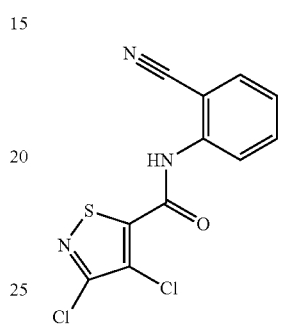

| | | |
|---|---|---|
| Ex B4 Fludioxonil | 200 | 70 |

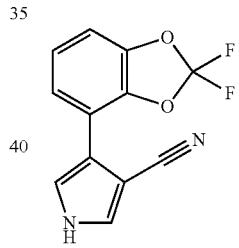

Inventive Compound Combination:

| | Ratio of the mixture | Rate of application of active compound in ppm | Actual efficacy | Expected value, calculated using Colby's formula |
|---|---|---|---|---|
| Ex I-2 + Ex B4 Fludioxonil | 1:1 | 200 + 200 | 88 | 75 |

The invention claimed is:

1. A composition comprising (A) at least one compound according to formula (I)

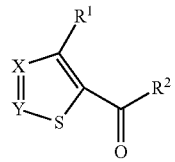

wherein
X is C-Hal,
Y is nitrogen,
R¹ is selected from the group consisting of hydrogen, halogen, $C_1$-$C_6$ alkyl substituted with Hal, $C_2$-$C_6$ alkenyl substituted with Hal, $C_3$-$C_6$ cycloalkyl substituted with Hal, and phenyl which is substituted with one or more substituents selected from the group consisting of halogen, cyano, and alkoxy,
R² is —NHC$_6$H$_5$ which is substituted with one or more substituents selected from the group consisting of cyano, halogen, $C_1$-$C_6$ alkyl, $C_1$-$C_6$ alkoxy, and $C_1$-$C_6$ alkylcarbonyl,
Hal is halogen,
and at least one fungicidally active compound (B) selected from the group consisting of Trifloxystrobin, Dimoxystrobin, Fluoxastrobin, Pyraclostrobin, and Picoxystrobin,
wherein (A) and (B) are the only active compounds in the composition and wherein the ratio of (A) to (B) is from 100:1 to 1:1.

2. The composition according to claim 1 wherein (A) R¹ is chlorine, R² is 2-cyanoaniline and Hal is chlorine, and (B) is trifloxystrobin.

3. The composition according to claim 1 wherein the ratio of (A) to (B) is from 100:1 to 10:1.

4. The composition according to claim 1 further comprising adjuvants, solvents, a carrier, surfactants or extenders.

5. A method for protecting a seed and/or shoots and foliage of a plant grown from the seed from damage by a pest or a fungus, comprising treating an unsown seed with the composition according to claim 1.

6. A method of treating seed comprising applying the composition according to claim 1 to said seed.

7. The method according to claim 6 wherein the seed is transgenic seed.

8. The composition according to claim 1 further comprising seed.

9. A method for controlling phytopathogenic fungi of plants or crops comprising applying (A) at least one compound according to formula (I)

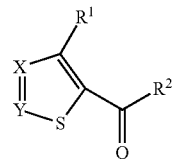

wherein
X is C-Hal,
Y is nitrogen,
R¹ is selected from the group consisting of hydrogen, halogen, $C_1$-$C_6$ alkyl substituted with Hal, $C_2$-$C_6$ alkenyl substituted with Hal, $C_3$-$C_6$ cycloalkyl substituted with Hal, and phenyl which is substituted with one or more substituents selected from the group consisting of halogen, cyano, and alkoxy,
R² is aniline —NHC$_6$H$_5$ which is substituted with one or more substituents selected from the group consisting of cyano, halogen, $C_1$-$C_6$ alkyl, $C_1$-$C_6$ alkoxy, and $C_1$-$C_6$ alkylcarbonyl,
Hal is halogen,
and at least one fungicidally active compound (B) selected from the group consisting of Trifloxystrobin, Dimoxystrobin, Fluoxastrobin, Pyraclostrobin, and Picoxystrobin,
to seed, to a plant, to fruit of the plant, to soil in which the plant is growing, or to soil from which the seed or the plant is grown; wherein (A) and (B) are the only active compounds applied to the seed, to the plant, to the fruit of the plant, to the soil in which the plant is growing, or to the soil from which the seed or the plant is grown, and wherein the ratio of (A) to (B) is from 100:1 to 1:1.

10. The method according to claim 9 comprising applying (A) and (B) simultaneously or sequentially.

11. The method according to claim 9 wherein a combination of (A) and (B) is applied at a rate of from 0.1 g/ha to 10 kg/ha for foliar treatment, or is applied at a rate of from 0.1 g/ha to 10 kg/ha for soil treatment, or is applied at a rate of from 2 to 200 g/100 kg of seed for seed treatment.

12. The method according to claim 10, comprising applying (A) and (B) simultaneously.

13. A composition comprising (A) isotianil and at least one fungicidally active compound (B) selected from the group consisting of Trifloxystrobin, Dimoxystrobin, Fluoxastrobin, Pyraclostrobin, and Picoxystrobin, wherein (A) and (B) are the only active compounds in the composition and wherein the ratio of (A) to (B) is from 100:1 to 1:1.

* * * * *